US005858762A

United States Patent [19]
Triplett

[11] Patent Number: 5,858,762
[45] Date of Patent: Jan. 12, 1999

[54] PLASMID FOR TRANSFORMATION OF ROOT NODULE BACTERIA

[75] Inventor: Eric W. Triplett, Madison, Wis.

[73] Assignee: Wisconsin Alumni Research Foundation, Madison, Wis.

[21] Appl. No.: 848,785

[22] Filed: May 1, 1997

[51] Int. Cl.⁶ ...................................................... C12N 1/20
[52] U.S. Cl. ..................... 435/252.3; 435/320.1
[58] Field of Search .............................. 435/252.3, 320.1, 435/69.1, 71.3, 172.3

[56] References Cited

U.S. PATENT DOCUMENTS

| 4,567,146 | 1/1986 | Brewin et al. | 435/172.3 |
| 5,183,759 | 2/1993 | Triplett | 435/252.2 |

OTHER PUBLICATIONS

Breil, Brenda T., et al., "DNA Sequence and Mutational Analysis of Genes Involved in the Production and Resistance of the Antibiotic Peptide Trifolitoxin," *Journal of Bacteriology*, pp. 3693–3702 (Jun. 1993).

Hungria, M., et al., "Relative efficiency, ureide transport and harvest index in soybeans inoculated with isogenic HUP mutants of *Bradyrhizobium japonicum*," *Biol. Fertil. Soils*, 7:325–329 (1989).

Johnson, Erik P., et al., "Plasmid RK2 Toxin Protein ParE: Purification and Interaction with the ParD Antitoxin Protein," *Journal of Bacteriology*, 178(5):1420–1429 (Mar. 1996).

Maier, Robert J., et al., "Toward More Productive, Efficient, and Competitive Nitrogen–Fixing Symbiotic Bacteria," *Critical Reviews in Plant Sciences*, 15(3):191–234 (1996).

Roberts, Richard C., "Definition of a Minimal Plasmid Stabilization System from the Broad–Host–Range Plasmid RK2," *Journal of Bacteriology*, 174(24):8119–8132.

Roberts, Richard C., "Characteristics and Significance of DNA Binding Activity of Plasmid Stabilization Protein ParD from the Broad Host–range Plasmid RK2," *The Journal of Biological Chemistry*, 268(36):27109–27117 (Dec. 25, 1993).

Sia, Elaine Ayres, et al., "Different Relative Importances of the par Operons and the Effect of Conjugal Transfer on the Maintenance of Intact Promiscuous Plasmid RK2," *Journal of Bacteriology*, 177(10):2789–2797 (May 1995).

Sobecky, Patricia A., et al., "Characterization of the Stable Maintenance Properties of the par Region of Broad–Host–Range Plasmid RK2," *Journal of Bacteriology*, 178(7):2086–2093 (Apr. 1996).

Weinstein, Michael, et al., "A Region of the Broad–Host–Range Plasmid RK2 Causes Stable In Planta Inheritance of Plasmids in *Rhizobium meliloti* Cells Isolated from Alfalfa Root Nodules," *Journal of Bacteriology*, 174(22):7486–7489, (Nov. 1992).

Triplett, Eric W., et al., "Trifolitoxin Production and Nodulation Are Necessary for the Expression of Superior Nodulation Competitiveness by *Rhizobium leguminosarum* bv. trifolii Strain T24 on Clover," *Plant Physiol.*, 85:335–342 (1987).

*Primary Examiner*—Nancy Degen
*Assistant Examiner*—Irem Yucel
*Attorney, Agent, or Firm*—Quarles & Brady

[57] ABSTRACT

A plasmid for use in root nodule bacteria is described which is intended both to increase yield of inoculated legume plants inoculated with the bacteria as well as aiding in the competitiveness of the bacteria with native strains. The plasmid include a hydrogen uptake element which aids in energy efficient nitrogen fixation by the plant bacteria symbiotic pair as well as a toxin and resistance element intended to aid in the competitive fitness of the inoculant bacterial strain.

9 Claims, 1 Drawing Sheet

PLASMID FOR TRANSFORMATION OF ROOT NODULE BACTERIA

CROSS-REFERENCE TO RELATED APPLICATIONS

This invention was made with United States government support awarded by the following agency: USDA AGRICREE No. 94-37305-0767. The United States has certain rights in this invention.

STATEMENT REGARDING FEDERALLY SPONSORED RESEARCH OR DEVELOPMENT

Not applicable.

BACKGROUND OF THE INVENTION

It has been well known for many years that leguminous plants are able to fix nitrogen from atmospheric nitrogen due to a symbiotic relationship between the plant and bacteria which dwell in nodules formed in the roots of the plants. The symbiotic root nodule bacteria are now classified in several separate genera, among them being Rhizobium, Bradyrhizobium, Sinorhizobium, and Azorhizobium. The four genera of nodule bacteria are characterized in part by the species of legume plants with which they are able to form the symbiotic nodulation relationship.

While significant research has been conducted on root nodulation bacteria in the hope of creating bacterial strains which will foster or improve the growth of legume plants cultivated agriculturally, the problem of increasing the effectiveness of inoculants of root nodule bacteria turns out to be a difficult one. In particular, for example, *Bradyrhizobium japonicum* strains, which are symbiotic with soybean, now are extent in soils throughout North and South America in those regions in which there has been historic soybean production, even though this species was originally indigenous only to Asia. The existing wild strains are the progeny of bacterial strains originally inoculated into soybean fields but which have now evolved to survive in these soils and climates. The existence of these bacterial strains in the agricultural soil ecosystem is a mixed blessing. These strains of Bradyrhizobium extent in most cultivation areas compete with intentionally inoculated Bradyrhizobium strains for occupation of the nodules of soybean plants, and while the presently extent or native species may be inefficient fixers of nitrogen, they are often superbly adapted for competitive root nodulation in the particular environment or microenvironment in which they now exist and thrive. Accordingly, creating newly improved root nodulation bacterial strains which are actually effective in the field as inoculants in increasing crop yield requires considerations of both increasing the effectiveness of the bacteria and also providing the improved or engineered bacteria with a mechanism by which they may compete effectively with bacterial strains now extent in most legume cultivation areas.

One of the characteristics of the nitrogen fixation process as performed by root nodulation bacteria is that a byproduct of the reaction is evolved hydrogen gas. For root nodule bacteria species which evolve hydrogen gas and release it into the atmosphere, a large amount of energy invested in the nitrogen fixation process is lost as the $H_2$ gas is released into the atmosphere. However, it has been found that some diazotroph, or nitrogen fixing, bacteria do not release $H_2$ even when nitrogen fixation is occurring. These bacteria were found to express an uptake hydrogenase enzyme which oxidized the hydrogen to release electrons. In the cases of some bacteria, the electron transport initiated by the hydrogenase reaction results in an efficient energy conserving electron transport chain, which results in recovery of most of the energy that would otherwise be lost in hydrogen production.

The multi-gene phenotype for hydrogen uptake, designated HUP, was found to exist in several species of root nodulation bacteria. However, many other root nodule bacterial strains and species do not contain this capability, and thus are relatively wasteful in their energy utilization compared to species which have the capability of HUP expression. For example, there are no known HUP positive strains of *Rhizobium etli* or *Bradyrhizobium elkanii*. It has also been found that strains of *Bradyrhizobium japonicum* which are HUP positive appear to be scarce in agricultural soils.

It has been proposed that the HUP genes can be introduced into root nodule bacteria not natively possessing this phenotype to aid in their agricultural utility. U.S. Pat. No. 4,567,146 discusses one strategy for this approach. However, the potential introduction widespread agronomic potential of uptake hydrogenase phenotype in bacterial strains faces several hurdles. Among them is the fact that the HUP positive inoculant strains must be competitive for nodulation with the endogenous strains now present in soils in crop growing areas. The HUP phenotype requires several genes and appears to be a competitive disadvantage in terms of metabolic burden to the bacteria. The second difficulty concerns the fact that there is an inherent instability in the expression of HUP phenotype in species which do not normally possess these genes. For example, Lambert et al., *Appl. Environ. Microbiol.*, 55:422–428 (1987), were able to engineer hup expression in *R. meliloti* strains by conjugation of a cosmid clone containing the hup region, from a species of *B. japonicum* which contained the hup region. However, the expression was transient in root nodules because the lack of proper partitioning of the plasmid during cell division in the absence of selection pressure. Addition of tetracycline or other selection antibiotics to commercial inoculants to prevent improper partitioning is expensive, unlikely to be efficient, and could result in modification of animal or soil plant pathogens due to antibiotic resistance, and hence is not practical.

Of course, even if the HUP phenotype can be engineered into a strain of bacteria, there is still the competitiveness problem. One strategy which has been discussed for this problem is to engineer the root nodule bacteria with a toxin which is inhibitory to other root nodule bacterial. U.S. Pat. No. 5,183,759 describes root nodule bacteria engineered to produce trifolitoxin, one such toxin.

In considering the problem of engineering root nodulation bacteria for uptake hydrogenase expression, another issue is the problem of strain by strain engineering of such bacteria. Now that the bacteria originally introduced as inoculants have evolved into discrete strains adapted to fit ecological conditions throughout agricultural regions it may be necessary for competitive reason to engineer different strains of bacteria for new traits for use in different agricultural regions of any given country or region. Accordingly, the ease with which the HUP phenotype can be transferred among bacterial strains becomes a critical question in the practical use of engineered nitrogen fixing root nodule bacteria for use on field crops.

BRIEF SUMMARY OF THE INVENTION

The present invention is summarized in that a plasmid for use in the transformation of root nodulation bacteria includes on it genetic cassettes capable of expressing the proteins necessary to confer upon a root nodule bacterial host strain the ability to produce hydrogenase and gain energy from hydrogen which would otherwise be lost during the diazotrophic process, together with a partitioning mechanism capable of ensuring that the plasmid is passed into progeny bacteria without the need for antibiotic resistance selection during microbial cultivation.

The present invention is also summarized in the plasmid which can be transferred into suitable Rhizobium or Sinorhizobium strains, and can confer upon those strains HUP positive phenotype so that they may more efficiently utilize the hydrogen created during the nitrogen fixation process, also conditions the expression of trifolitoxin antibiotic production and trifolitoxin resistance.

It is a feature of a plasmid constructed in accordance with the preferred embodiment of the present invention that the plasmid can be readily shuttled among Rhizobium and Sinorhizobium strains by conjugation or transformation.

Other objects, advantages, and features of the present invention will become apparent from the following specification.

DETAILED DESCRIPTION OF THE INVENTION

Figure 1:
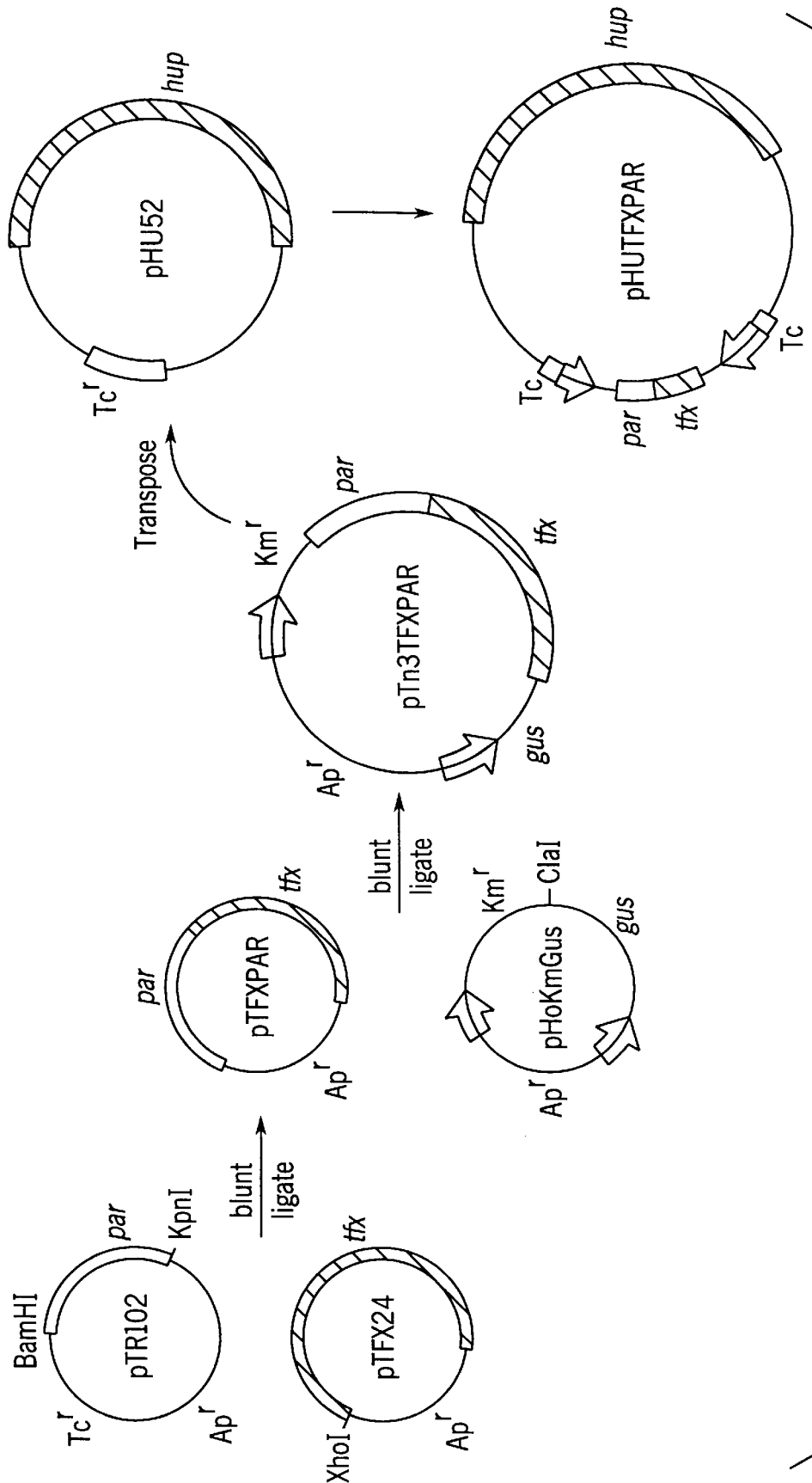
FIG. 1 is a schematic illustration of plasmid manipulation in an example of the present invention.

In accordance with the present invention, a plasmid is constructed which may easily be transferred among various strains of Rhizobium and Sinorhizobium bacteria by conjugation. This plasmid confers upon those bacterial strains harboring the plasmid both the ability to increase the effective yield of leguminous plants with which the root nodule bacteria form the symbiotic relationship as well as conferring upon the root nodule bacteria a competitive advantage in gaining occupancy of the nodules as compared to other bacterial strains presently native to the field environments.

The plasmid in accordance with the present invention achieves this advantage by combining several disparate features. The first is that the plasmid contains all of the necessary genes in order to express the hydrogen uptake, or HUP, phenotype so that the bacteria harboring the plasmid will recover energy from evolved hydrogen which would otherwise be wasted during the nitrogen fixation process. Secondly, the plasmid contains a locus which prevents incorrect partitioning of the plasmid in progeny bacteria, thereby ensuring that the presence of the HUP phenotype in daughter bacterial cells is maintained as the bacteria propagates throughout its environment. Thirdly, the bacteria contains an expression cassette encoding the antibiotic peptide trifolitoxin so as to confer upon strains harboring the bacteria a competitive advantage in gaining nodule occupancy compared to other Sinorhizobium or Rhizobium bacterial strains due to the production of both the antibiotic and the inheritance of the resistance gene to that antibiotic. In this way, stable strains of Rhizobium or Sinorhizobium can readily be created which are both competitive and which are capable of enhancing the effective yield from the leguminous plant grown in symbiotic relationship with those bacteria.

Plasmids incorporating the HUP phenotype have previously been described in the literature. A vector known as pHU52 is described in Lambert et al., *Appl. Environ. Microbiol.*, 53:2:422–428 (1987). The plasmid HUP pHU52 is a large plasmid containing all of the genes necessary for hydrogen uptake (hup) as well as the genetic sequences necessary to utilize the evolved hydrogen in energy storage in the plant. The multigene components which confer the HUP+ phenotype is so large (>20 kb) that insertion of them into the bacterial genome is difficult to achieve. The size of the elements also ensures that plasmids carrying these elements are large and susceptible to loss during inheritance. To engineer new plasmids with this phenotype is also a non-trivial problem. One approach to this problem is to consider adding any additional genetic elements needed into a HUP+ plasmid, such as pHU52. The problem then simply becomes how to insert the other desired genetic components into this plasmid backbone without disrupting the efficient functioning of the HUP genes. One strategy for accomplishing this objective is to use the tetracycline resistance locus located in pHU52 and direct insertion of foreign DNA into that locus to ensure that none of the genes in the complex HUP operon are disrupted by the insertion. This has the additional benefit of disrupting the tetracycline resistance trait which might pose a hurdle in regulatory approval of use of an engineered plasmid in the environment. Thus it is more convenient first to combine the other elements desired in the plasmid, specifically the gene cassette encoding trifolitoxin and the resistance to it as well as the partitioning genes, and that genetic cassette may be inserted into the desired locus in the large pHU52 plasmid using a transposable element.

The partitioning element of the present invention is intended to prevent daughter microbial cells, following asexual reproduction of the bacterial strain carrying the plasmid, from failing to inherit the desired phenotype. The par element chooses for the embodiment described here is a locus from an *E. coli* plasmid designated RK2 described by Roberts and Helinski in *Jour. Bact.* 174:24:8119–8132 (1992) and Sia et al., *Jour. Bact.* 177:10:2789–2797 (1995). The RK2 par element contains several genes in at least two operons which has the effect of stabilizing plasmids within a bacteria hosting the plasmid. A plasmid containing the par element is exquisitely stable in maintenance during unselected growth due to the presence of the plasmid. Apparently the RK2 par element inhibits the growth of plasmidless segregants, and thus ensures that all surviving daughter cells contain the entire plasmid into which the par locus is inserted.

It of course a requirement of a plasmid for use in a Rhizobium or Sinorhizobium species that the plasmid have a competent replication origin and have genetic elements capable of expression in the bacterial host into which the plasmid is inserted. Since all the genetic elements described in the construction of this plasmid come from root nodulation bacteria, with the exception of the par locus, it is not believed that this is a problem. The RK2 par locus originates from *E. coli*, but is already known to work in Sinorhizobium, Weinstein et al., *J. Bacteriol.*, 174:7486–7489 (1992).

A plasmid constructed as described here can be readily transferred by conjugation among strains of root nodule bacteria. Since virtually all known isolates of bacteria which infect clover (*R. leguminosarum bv. trifolii*), alfalfa (*S. meliloti*), and common bean (*R. leguminosarum bv. phaspoli, R. efli,* and *R. tropici*) lack the uptake hydrogenase, this permits the advantages of this phenotype to be used with these crop species effectively for the first time.

EXAMPLE

To begin the construction of the plasmid embodying the present invention, a 32 kb par locus was isolated from the plasmid RK2 described by Weinstein et al. in *J. Bacteriol.* 170:7486–7489 (1992). The par locus from RK2 forces complete plasmid partitioning during cell division by five genes encoded in the plasmid by two divergently transcribed operons. Each of the two operons codes for an independent mechanism to ensure plasmid stability. The first operon, designated par CBA includes a resolvase mechanism while the par DE operon includes a toxin, referred to as par E and antitoxin (par D) mechanism. The par locus confers plasmid stability regardless of the replicon containing the 3.2 kilobase region and has been shown to confer complete plasmid stability with *Sinorhizobium meliloti* during root nodule development.

It was necessary to find a practical way to insert the 3.2 kb par locus into pHU52. It was decided that the most practical way to accomplish this is to insert the par locus within the inverted repeats of a transposon which had inserted itself in a locus in the pHUP52 plasmid without disrupting anything needed. Then the par locus could be transposed into the transposon itself on pHUP52. It was decided to insert the transposon in the tetracycline resistance gene in pHV52. By providing a transposase in trans, one can insure that the par locus will not transpose out of pHU52 once it has been inserted. In addition, as the Tn3 transposon was chosen for this work also contains a kanamycin resistance gene, it is possible to select for pHU52 after interruption of the tetracycline resistance gene using kanamycin selection. The proper insertions were ampicillin resistant, from a gene carried with the trifolitoxin cassette, and tetracycline sensitive due to the insertion at the proper locus. This construction of the transposable par locus has been completed. The transposition of the par locus into pHU52 has been completed. This construct is characterized by the trifolitoxin gene and the par locus inserted into and disrupting a gene for tetracycline resistance.

To confer trifolitoxin expression onto the same plasmid, it was decided that the par locus would be inserted adjacent to the gene encoding trifolitoxin, tfx, which could then be inserted into the inverted repeats of Tn3 in the backbone of pHU52. Thus, the par-tfx construct was constructed first within the inverted repeats of Tn3. This process is illustrated in FIG. 1.

In FIG. 1 a plasmid designated pTR102 contains the par locus. A second plasmid, designated pTFX24 contains the complete gene sequences for the trifolitoxin and its resistance gene. The plasmid pTR102 was digested with BamHI and KpnI, and a 3.2 KB fragment containing the par locus was recovered. The 3.2 KB fragment was ligated into the unique XhoI site of the plasmid pTFX24, which lies adjacent to the region encoding the trifolitoxin gene, by blunt end ligation. The resulting plasmid is designated pTFXPAR in FIG. 1. That plasmid was then digested with ApaI and SacI, and a 10.4 kb fragment containing the TFX-PAR loci was then cloned by blunt end ligation into the unique Cla I site found within the inverted repeats of Tn3 recovered from a plasmid known as pHoKmGUS, as described by Breil et al. *J. Bacteriol.* 178:4150–4156 (1996). The transposon was then used to hop the TFX-PAR locus into the tetracycline resistance locus contained within pHU52 using a transposase provided in trans from the plasmid pSshe. The resulting combined plasmid designated pHUTFXPAR confers trifolitoxin production and resistance, hydrogen recycling, and complete plasmid stability in culture and in nodules on any bacterium harboring this plasmid. This plasmid pHUTFXPAR can be conjugated or transformed into any strain of Rhizobium or Sinorhizobium to confer upon that plasmid both increased efficacy as a symbiont as well as enhanced competitiveness for nodule occupancy in the field.

It is expected that Rhizobium or Sinorhizobium strains containing plasmid pHUTFXPAR will increase the yield of crop plants grown in fields into which these strains are inoculated. The trifolitoxin production phenotype will confer on the strains competitiveness with native strains of these species. The HUP+ phenotype will aid the energy utilization of the symbiotic plant and bacteria combination. The RK2 par locus will ensure that these traits are maintained in the strain during propagation. Thus a useful and improved root nodule bacteria inoculant is formed.

The success of inoculant bacterial strains carrying a plasmid such as pHUTFXPAR can be demonstrated by field trials which will demonstrate that crop plants, such as alfalfa, inoculated with suitable strains of bacteria harboring the plasmid (*R. meliloti* for alfalfa) will show increased plant biomass yield as compared to controls without the advantageous combination of genetic elements.

To assist in the practice of one embodiment of the present invention, copies of the plasmid pHUTFXPAR have been deposited with the American Type Culture Collection, currently located at 10801 University Boulevard, Manassas, Va., USA, on Apr. 30, 1997, with accession no. ATCC 98419. This deposit is under conditions of the Budapest Treaty. A taxonomic description of this deposit is pHUTFXPAR in *E. Coli* C2110.

I claim:

1. A plasmid comprising a genetic element which expresses uptake hydrogenase activity in a root nodule bacterial strain, a genetic element which expresses trifolitoxin production and resistance in a root nodule bacterial strain, a partitioning element which has the effect of ensuring that the plasmid is inherited by viable daughter cells following asexual reproduction of a root nodule bacteria harboring the plasmid, and an origin of replication effective in root nodule bacteria.

2. A plasmid as claimed in claim 1 wherein the genetic element for hydrogenase is the hup locus for pHU52.

3. A plasmid as claimed in claim 1 wherein the genetic element for trifolitoxin is the tfx element from pTFX24.

4. A plasmid as claimed in claim 1 wherein the partitioning element is from the plasmid RK2.

5. A plasmid as claimed in claim 1 wherein the plasmid further comprises a gene for tetracycline resistance and the genetic element for trifolitoxin production is inserted into and disrupts the gene for tetracycline resistance.

6. A root nodule bacteria strain harboring a plasmid according to claim 1.

7. A root nodule bacteria strain as claimed in claim 5 wherein the bacteria strain is selected from the group consisting of Rhizobium, Sinorhizobium, and Azorhizobium.

8. A legume seed inoculum comprising a suitable carrier and the bacterial strain of claim 6.

9. Plasmid pHUTFXPAR.

* * * * *

UNITED STATES PATENT AND TRADEMARK OFFICE
CERTIFICATE OF CORRECTION

PATENT NO. : 5,858,762
DATED : January 12, 1999
INVENTOR(S) : Eric W. Triplett

It is certified that error appears in the above-identified patent and that said Letters Patent is hereby corrected as shown below:

At column 5, line 22, change [pHV52] to --pHUP52--.

Signed and Sealed this

Sixth Day of July, 1999

Attest:

Q. TODD DICKINSON

Attesting Officer

Acting Commissioner of Patents and Trademarks